(12) United States Patent
Robertson et al.

(10) Patent No.: US 6,605,468 B1
(45) Date of Patent: Aug. 12, 2003

(54) METHOD AND MEDIUM FOR IN VITRO CULTURE OF HUMAN EMBRYOS

(75) Inventors: Sarah Robertson, St Peters (AU); Matts F. Wikland, Göteborg (SE); Cecilia Sjoblom, Göteborg (SE)

(73) Assignees: Luminis Pty Ltd. (AU); Fertilitescentrum AB (SE)

( * ) Notice: Subject to any disclaimer, the term of this patent is extended or adjusted under 35 U.S.C. 154(b) by 0 days.

(21) Appl. No.: 09/720,231

(22) PCT Filed: Jun. 18, 1999

(86) PCT No.: PCT/AU99/00499

§ 371 (c)(1),
(2), (4) Date: Feb. 20, 2001

(87) PCT Pub. No.: WO99/67364

PCT Pub. Date: Dec. 29, 1999

(30) Foreign Application Priority Data

Jun. 19, 1998 (AU) .............................................. PP4212

(51) Int. Cl.[7] ............................ C12N 5/00; C12N 5/08; C12N 5/10; A61B 17/43; A61D 7/00
(52) U.S. Cl. ....................... 435/385; 435/366; 435/363; 435/383; 435/384; 600/33
(58) Field of Search ....................... 800/8, 14; 435/70.1, 435/40, 70.3, 405, 385, 366, 363, 383, 384; 600/33

(56) References Cited

U.S. PATENT DOCUMENTS 5,670,351 A * 9/1997 Emerson et al. .......... 435/172.3
5,744,361 A * 4/1998 Hoffman et al. ............ 435/372

OTHER PUBLICATIONS

Loutradis et.al.; Biological Factors in Culture Media Affecting in Vitro Fertilization, Preimplantation Embryo Development, and Implantation, 2000, Annakls Academy of Sciences: 325–335.*

Genzyme Diagnostics; 1995, Colony Stimulating Factors: 156–160.*

Moraes, Alice A.S. de Moraes and Hansen, Peter J. "Granulocyte–Macrophage Colony–Stimulating Factor Promotes Development of In Vitro Produced Bovine Embryos" *Biology of Reproduction*, 57: 1060–1065, 1997.

Jokhi, P.P., King, Ashley, and Loke, Y.W. "Production of Granulocyte–Macrophage Colony–Stimulating Factor by Human Trophoblast Cells and by Decidual Large Granular Lymphocytes" *Human Reproduction*, 9(9): 1660–1669, 1994.

Haimovici, Florina, Hill, Joseph A., Anderson, Deborah J. "The Effects of Soluble Products of Activated Lymphocytes and Macrophages on Blastocyst Implantation Events In Vitro" *Biology of Reproduction*, 44: 69–75, 1991.

J. Martal et al. "Recent Developments and Potentialities for Reducing Embryo Mortality in Ruminants: The Role of IFN-τ and Other Cytokines in Early Pregnancy" *Reproduction, Fertility and Development*, 9: 355–380, 1997.

M. I. Garcia–Lloret et al. "Demonstration of Functional Cytokine–Placental Interations: CSF–1 and GM–CSF Stimulate Human Cytotrophoblast Differentiation and Peptide Hormone Secreation" *Experimental Cell Research*, 214:46–54, 1994.

* cited by examiner

*Primary Examiner*—Deborah Crouch
*Assistant Examiner*—Thai-An N. Ton
(74) *Attorney, Agent, or Firm*—Henry D. Coleman; Coleman, Sudol, Sapone, P.C.

(57) ABSTRACT

Disclosed is a medium for the propagation of early stage embryos to blastocyst stage. The medium contains an effective amount of GM-CSF to increase the percentage of pre-blastocyst embryos which develop to transfer ready blastocysts. Also disclosed is a method of growing early stage human embryos to transfer ready blastocysts. The method includes the step of incubating the embryos in vitro in a culture medium containing an effective amount of human GM-CSF for a time and under conditions to increase the proportion of transfer ready blastocysts. An IVF program that includes the method of growing early stage human embryos to transfer ready blastocysts is also disclosed.

20 Claims, 3 Drawing Sheets

METHOD AND MEDIUM FOR IN VITRO CULTURE OF HUMAN EMBRYOS

RELATED APPLICATIONS

This application is a §371 national phase filing of PCT/AU99/00499, having an international filing date of Jun. 18, 1999.

Infertility is a great concern to many couples who wish to conceive. The proportion of couples that are unable to conceive naturally is remarkably high. In the USA it is said that some 10–15% of couples of reproductive age are unable to have children, whereas in the United Kingdom the proportion has been estimated at 14%.

In the last 20 years or so some hope has been held out to infertile couples with the development of in vitro fertilisation (IVF) techniques. These IVF techniques generally take the form of stimulating the female to ovulate, contacting collected ova with sperm in vitro and introducing fertilised ova into the uterus. Multiple variations of this general process also exist. Despite considerable research and technical advances in the IVF field the rate of successful pregnancy following IVF treatment is still quite low and is in the order of 15 to 25% per cycle.

Undertaking an IVF program often causes great anguish, especially where there is no resultant successful pregnancy. It is presently believed that the poor success rate for IVF treatment is due to an extraordinarily high rate of early embryonic loss or implantation failure (Weinberg et al., 1988; Lenton et al., 1988).

The low efficacy of IVF, together with its high cost and the associated psychological trauma from repeated treatment failures make it desirable that improvements are made to the procedure. Current methods of increasing pregnancy rates during IVF treatment include placing multiple embryos (2–5) into the uterine cavity. This is not always successful and also carries with it a higher risk of multiple pregnancy.

In most in vitro fertilisation units embryos are transferred to the uterus 2 days after fertilisation (4–8 cells). One view is that the use of embryos at this early stage may contribute significantly to the low pregnancy outcome of IVF programs and that it is more desirable to use embryos at the blastocyst stage reached at day 5–7 of culture. The advantages suggested include improved synchronisation between embryo and uterus and the ability to select better quality embryos over the longer culture period. Blascocyst transfer may also help reduce the number of multiple births resulting from IVF, through allowing the selection of fewer numbers of highly competent embryos per transfer.

Unfortunately in standard culture media the majority of embryos (about 75%) fail to develop beyond the 4–8 stage. Nevertheless with certain clinical indications implantation of human embryos is performed at the blastocyst stage despite the low proportions of embryos that develop to blastocyst. Some recent studies have used co-culture techniques whereby embryos are co-cultured with feeder cells, for example Vero cells, which technique can more than double blastocyst formation rates (Ménézo et al., 1990; Plachot et al., 1995). There have been a number of studies using these co-culture techniques which have shown increased implantation rates after blastocyst transfer (Ménézo et al., 1992), particularly in women with repeated previous implantation failures (Oliveness et al., 1955; Plachot et al., 1955).

Co-culture is time consuming and expensive and concerns have been expressed about possible transfer of disease from contaminated cultures (Oliveness et al., 1955), in particular there is a concern relating to viral contamination which contamination is considered to be virtually impossible to fully eliminate. A safer and more practical approach is to attempt to produce a culture medium able to sustain embryo development through to the blastocyst stage that is independent of co-culture.

One approach to enhance in vitro embryo development without using co-culture techniques is to attempt to define factors that might be used to enhance embryo development in in vitro culture. A number of attempts have been already made to identify factors that might assist and amongst the promising factors are various stimulatory factors known as cytokines. One such factor, leukemia inhibitory factor (LIF) has already been indicated as being positive in this regard for humans (Dunglison et al 1996) and livestock species, U.S. Pat. No. 5,418,159.

One of the many factors also currently under investigation in both animals and humans relative to conception and embryo development is granulocyte-macrophage colony-stimulating factor (GM-CSF). However to date there has been no definite indication that a medium supplemented with GM-CSF would be sufficient to enhance the in vitro development of embryos to the blastocyst stage in a defined culture medium.

GM-CSF is a 23–29 kD glycoprotein which although secreted in a soluble form in vitro, is one of many cytokines known to be sequestered and immobilised in the ECM (extracellular matrix) in vivo through association with heparan sulphate. GM-CSF was originally characterised as a hemopoietic regulator and determinant of the maturation and behaviour of myeloid leukocytes in peripheral tissues. It is now known that GM-CSF is produced by a diversity of cell types including T-lymphocytes, monocytes, macrophages, fibroblasts, endothelial cells and epithelial cells.

The uterine epithelium has been identified by in situ hybridisation and in in vitro cell isolation studies as a major source of GM-CSF in the mouse uterus (Robertson el al 1992, Robertson et al 1994) and human oviduct and uterus (Zhao and Chegini 1994, Giacomini et al 1995). A role for GM-CSF in reproductive processes was supported by studies perturbing the cytokine environment during early pregnancy in vivo (Tartakovsky and Ben Yair, 1991) and experiments showing impaired fertility in genetically GM-CSF deficient mice (Robertson et al 1999).

Studies of radio-labelled ligand binding show clearly that murine blastocysts bind $^{125}$I-GM-CSF specifically, indicating that they express at least the low affinity form of the GM-CSF receptor. This conclusion was supported by RT-PCR analysis, which showed that blastocysts express mRNA for the α-subunit of the GM-CSF receptor complex. A similar situation was found to exist in human embryos. GM-CSF-R was expressed at similar levels through the first four days of murine and human embryo development, from fertilisation to blastocyst stage. However mRNA for the β-subunit of the GM-CSF receptor complex was not detected in embryos of either species by the RT-PCR technique. Together, these data suggest that embryos express GM-CSF receptor from at least as early as fertilisation, but that it may be of the low affinity form. The embryo therefore falls into the same category as endothelial cells and other non-hemopoietic cells which exhibit a biological response to GM-CSF despite expressing only low affinity receptors. Although it seems clear in hemopoietic cells that the α-subunit of the GM-CSF receptor cannot on its own transduce proliferative signal, it is not known whether the α-subunit can in some circumstances initiate responses in cells in the absence of the β-subunit. The recent discovery of unconventional forms of the GM-CSF receptor in the human suggests that this may be possible.

It has also been shown that binding of cognate ligands to the GM-CSF receptor a subunit in isolation may mediate increased glucose transport via a phosphorylation-independent pathway (Ding et al., 1994). Recent experiments by the inventor show that culture with recombinant mouse GM-CSF (mGM-CSF) stimulates increased glucose uptake in murine blastocysts, to an extent achievable with known glucose transport stimulants such as insulin-like growth factor-1, suggesting that this cytokine may stimulate metabolism in murine embryos.

There is some evidence to indicate that GM-CSF also participates in regulation of embryonic growth. Conditioned media rich in mGM-CSF have been found to be effective particularly in promoting blastocyst development, particularly in the attachment of hatched blastocysts to serum attachment factors in plastic culture dishes (Robertson et al., 1991). The media was conditioned by cells from LPS activated mouse lung tissue, and contains a number of other factors which could contribute to the embryotrophic activity.

In further studies by the inventor one cell and eight cell mouse embryos were cultured with or without recombinant mouse GM-CSF (rm GM-CSF) in a defined medium, and again there was a significant increase in the rate at which hatched blastocysts attached to the culture dish. The proportion of embryos developing to eight cell or blastocyst stage was not altered by cytokine. The rate at which embryos developed to blastocysts and hatched from the zona pellucida was also similar, regardless of whether cytokine was present or absent.

In further experiments the survival and/or proliferation of blastomeres within developing mouse blastocysts, particularly inner mass cells, was shown to be enhanced by exposure to native GM-CSF in vivo, or by recombinant GM-CSF in vitro (Robertson et al., 1998).

Several groups have reported both positive and negative effects of GM-CSF on various stages of early embryo development. Hill et al. (1987) have found that GM-CSF at high doses (>1000 U/ml) inhibited the development of 2-cell embryos into morulae. In two studies, ectoplacental cone trophoblast has been found to proliferate in response to GM-CSF (Armstrong and Chaouat 1989; Lea and Clark 1993), but in the second instance an effect was obtained with native but not recombinant cytokine. Haimovoci et al. (1991) found that 250 U/ml or more of GM-CSF inhibited the attachment of blastocysts to fibronectin-coated culture dishes in the absence of serum. Lea and Clark (1993) have reported that recombinant GM-CSF (at between 10 and 100 U/ml) inhibited the incorporation of $^3$H-thymidine into outgrowing, implanted blastocysts, in a dose dependent manner. Tartakovsky and Ben-Yair (1991) found that systemic GM-CSF administration markedly enhanced early embryonic development in vivo, but did not note any effect of GM-CSF on embryonic development in vitro. These results are difficult to reconcile. However, the differences are likely to be related to the developmental stages examined, the methods for embryo culture, the strains of mice, and the sources and concentrations of cytokine used. For example, some cytokine preparations may contain potentially embryotoxic contaminants such as endotoxin. In addition, there is emerging evidence that there may be more than one mechanism by which GM-CSF is able to exert its effects in target cells, and it is possible that the glycosylation state of the cytokine (which would also be dependant upon its source) may be important for binding to unconventional receptors.

A study of bovine embryos (de Moraes and Hansen 1997) used recombinant bovine GM-CSF (rbGM-CSF) in attempt to enhance embryo development to blastocyst stage. The rbGM-CSF only had a significant impact on the proportion of embryos developing to blastocyst stage at very high levels of 10 ng/ml, and the numbers of embryos tested were relatively low so the results might be viewed with some concern. Additionally it was found however that the proportion of blastocysts that expanded or hatch dropped significantly with the 10 ng/ml rbGM-CSF and 1 ng/ml rbGM-CSF and thus can be seen an adverse effect on the capacity of the blastocysts to be used subsequently as their development had essentially terminated in vitro.

SUMMARY OF THE INVENTION

The present invention results from a finding that recombinant human GM-CSF (rhGM-CSF) is effective at substantially increasing the proportion of early embryos that develop to blastocyst and increasing the proportion of those embryos that continue to expanded blastocyst and then hatched blastocyst stages of development. The net result is that a much greater proportion of embryos can now be grown to blastocyst stage and used for implantation in an IVF program in humans.

This contrasts with the mixed findings in other species, whereby only moderate and inconsistent effects on development to blastocyst stage and beyond were reported.

This finding bas implications in the formulation of media for use in in vitro culturing of embryos to blastocyst stage and in methodologies of growing such embryos and in the manner in which IVF programs are conducted. It is anticipated that this invention will lead to a greater success rate in such IVF programs.

Thus in one broad form of a first aspect the invention could be said to reside in a medium for propagation of early stage embryos to blastocyst stage, said medium containing an effective amount of human GM-CSF to increase the percentage of pre-blastocyst embryos which develop to transfer ready blastocysts.

Transfer ready blastocysts are embryos developed to the stage where a blastoceol cavity is clearly evident and comprises greater than 50% of the volume of the embryo. This stage would in the in vivo situation normally be achieved 4–5 days after fertilisation, soon after the embryo has traversed to fallopian tube and arrives in the uterus.

In one form the medium is a serum deprived medium. The serum deprived medium is desirable in so far as the risk of contamination is drastically reduce The term serum deprived when used in this specification refers to a medium that does not include serum, or any partially defined serum fraction as an additive, but may include a medium that includes serum derived components that have been substantially purified from serum, and may or may not have been modified.

In another form the medium might be a fully defined medium.

Most preferably the human GM-CSF is in purified form, and most preferably purified in from a non-animal and nonhuman source, and might thus be purified from a recombinant micro-organism.

The GM-CSF receptors of embryos appears to be somewhat unique in composition compared to GM-CSF receptors elsewhere and it is therefore likely that the support for embryo growth may not require a fully native GM-CSF. The hGM-CSF may thus be modified or altered in any one of a number of ways and may or may not need to be glycosylated. The hGM-CSF may be truncated, include amino acid deletions and substitutions or may be a recombinant molecule with another growth factor such as perhaps LIF.

Where rhGM-CSF is used it is anticipated that the level of rhGM-CSF in the medium as used will be approximately 1 ng/ml which a physiologically normal level. However, ranges of concentration are also possible and it is anticipated that concentrations ranging from about 0.01 ng/ml to about 5 ng/ml will also give an increase depending on the specific activity of the recombinant or native GM-CSF preparation. It will be understood however that it might be found that concentrations outside of this might also lead to a beneficial effect.

A base medium to which the hGM-CSF is added might be any one known to the person skilled in the art.

The media in which this invention might be used can be any media suitable for use for the in vitro support of embryo development and growth. These media might include but are not limited to HTF medium (Quinn, 1985a), IVF50 (Scandinavian IVF Science), S2 (Scandinavian IVF Science), G1.2 (Scandinavian IVF Science), G2.2 (Scandinavian IVF Science) which references are incorporated herein by references in relation to the media.

In a broad form of a second aspect, the invention could be said to reside in a method of growing early stage human embryos to transfer ready blastocysts, including the step of incubating the embryos in vitro in a culture medium containing an effective amount or human GM-CSF for a time and under conditions to increase the proportion of transfer ready blastocysts.

It is anticipated that the early stage embryos will generally be contacted with GM-CSF at an early stage. The early stage of the embryos may be from immediately after fertilisation, through to several days after fertilisation but preferably before 4 days. Most preferably the contact will be within 2 days of fertilisation. It will be understood that these will be at the 2–16 cell, morula or pre-blastocyst. Generally a 1 day embryo will have 2 cells, 3 day is 16 cell or morula and in 4 to 5 days will develop to a blastocyst. A blastocyst is characterised by a clearly visible blastoceol cavity.

It is anticipated that the in vitro growth will be continued until the blastocysts reach the day 5 to 6 stage, however, in certain embodiments of the invention the culturing of the embryo may be to an earlier, or later stage.

In one form this second aspect of the invention comprises culturing of the embryo in a serum deprived medium including human GM-CSF until blastocyst stage is reached, and then transferring to a second medium including human GM-CSF for further culturing In a broad form of a third aspect the invention could be said to reside in an IVF program comprising the steps of:
  contacting an human egg with a human sperm to form a conceptus
  growing the resulting conceptus at least after the 8 cell stage embryo has formed in vitro in a defined culture medium containing an effective amount of human GM-CSF for a time and under conditions to increase the chance of achieving a transfer ready blastocyst
  transferring the transfer ready blastocyst into a compatible human uterus For a better understanding, the invention will now be described with reference to a number of examples.

DETAILED DESCRIPTION OF THE INVENTION

EXAMPLE 1

Measurement of Embryonic Viability and Development

Materials and Methods

Figure 1:
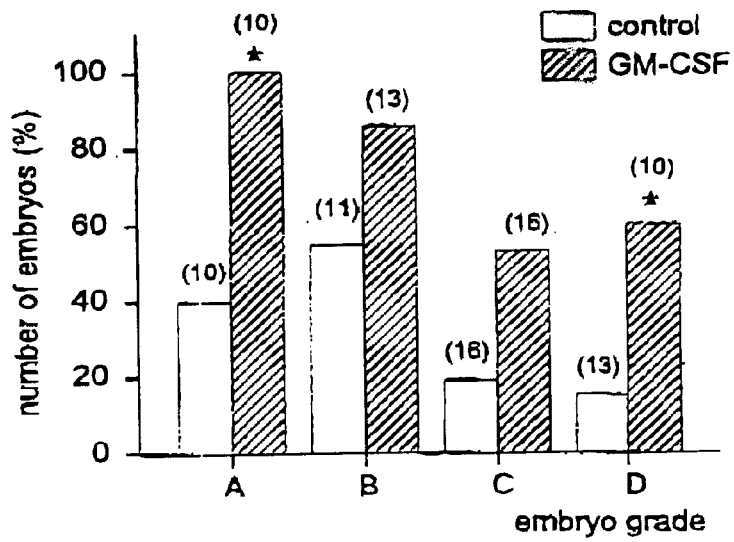
FIG. 1: Effect of GM-CSF on development of embryos to blastocysts, according to embryo grade. Data is the number of embryos developed to blastocyst from experiments 1, 2 and 3 combined, expressed as a percentage of the initial number of cleaved (2–4 cell) embryos. The number of embryos in each group are given in parentheses.

The embryos used in this study were donated by couples undergoing IVF treatment at Fertilitetscentrum AB, Göteborg, Sweden. Embryos frozen at the 2–4 cell stage were thawed at or beyond their one year storage limit in liquid nitrogen. Ethics approval for the study was obtained from the research ethics committee at University of Göteborg (number 700-96).

Ovarian Stimulation and in Vitro Fertilisation

Patients received 300 µg buserelin gonadotrophin-releasing hormone agonist (GnRHa; Suprecur; Hoechst, Frankfurt, Germany) three times daily intranasally, starting 1 week before expected menses and lasting for two weeks. Down-regulation was confirmed by a serum estradiol content of <0.2 nmol/l. Patients were then given recombinant follicle stimulating hormone (r-FSH; Gonal-F; Serono Laboratories, Aubonne, Switzerland; 150–225 IU/day subcutaneously). The starting dose was dependent on the patient age and/or previous response during ovarian stimulation (Wikland et al., 1994). The ovarian response was monitored by ultrasound and serum estradiol levels as previously described (Bergh et al., 1997). GnRHa and rFSH were administered until there was at least one follicle >18 mm in mean diameter and two others >16 mm. Finally, oocyte maturation was triggered by one sub-cutaneous injection of 10 000 IU of hCG (Profasi; Serono Laboratories).

Oocytes were retrieved 36–38 h after hCG administration, assessed morphologically and fertilised in vitro. The embryos were cultured in IVF-50 (Scandinavian IVF Science AB, Göteborg, Sweden) and frozen on day 2 using a 3-step propanediol cryo-preservation kit (Freeze Kit 1, Scandinavian IVF Science) according to the manufacturers instructions.

Recombinant GM-CSF

Recombinant human (rh)GM-CSF was obtained from R&D Systems Europe Ltd, Oxon, UK. The biological activity of the recombinant cytokine preparations was measured in a bioassay employing a GM-CSF responsive cell line (human myeloid TF-1 cell line), essentially as described by (Kitamura et al. 1989). Duplicate serial 1:2 dilutions were incubated with 2000 TF-1 cells in 200 ul of RPMI-1640 (Gibco) supplemented with 10% fetal calf serum (FCS; Commonwealth Serum Laboratories, Australia), $5 \times 10^{-5}$ M β-mercaptoethanol and antibiotics. After 2 days, cultures were pulsed with 1 uCi of $^3$H thymidine (Amersham, Arlington Heights, Ill.) for 6 hours, harvested onto glass fibre paper using a Titretech automated cell harvester and radioactivity measured in a liquid scintillation beta counter.

Embryo Thawing, Allocation and Culture

Frozen 2–4 cell embryos were thawed in four steps using a propanediol method for embryo thawing (Thaw Kit 1, Scandinavian IVF Science) following instructions given by the manufacturer. The viable embryos were classified and graded according to criteria listed in Table 1.

TABLE 1

Embryo classification criteria

| Embryo Grade | Morphology |
|---|---|
| A | Regular blastomeres without fragments |
| B | Regular or irregular blastomeres, up to 30% fragments |
| C | Regular or irregular blastomeres, more than 30% fragments |
| D | 50% of the blastomeres dead after thawing |

To avoid bias the embryos were randomly allocated, with regard to patient and embryo grade, into the different culture groups (Table 2). The embryos were cultured in groups of five embryos per drop. To avoid the toxic effects of ammonium, released due to metabolism and breakdown of amino acids, the culture media was renewed every 48 h until hatching occurred. In two experiments the embryos were cultured in 20 μl drops of IVF-50 (Scandinavian IVF Science) containing 2 ng/ml rhGM-CSF (diluted 1:25 000 from stock material) or carrier (2 ng/ml BSA, diluted 1:1 000 from stock material). Culture drops were covered by 4 ml Ovolil-200 (Scandinavian IVF Science) in Falcon 3004 dishes (Becton-Dickinson Labware, Franklin Lakes; N.J., USA). When blastocysts were detected these were transferred into 1 ml of S2 (Scandinavian IVF Science) in Falcon 3037 dishes, containing 5% FCS and 2 ng/ml rhGM-CSF or carrier. Developmental stage was scored every 8 h from thawing until 2300 h on day 8 (200 h post-insemination).

In a third experiment the embryos were transferred from IVF-50 into S2 medium (Scandinavian IVF Science) at the 6–8 cell stage. Additions of GM-CSF and carrier were the same as in the two previous experiments. When blastocysts were detected they were transferred to Falcon 3037 dishes, coated 24 h previously with Biomatrix EHS (Boehringer Ingelheim Bioproducts, Heidelberg, Germany). Developmental stage was scored every 8 h from thawing until 2300 h on day 8 (200 h post-insemination). Embryo scoring in each of the experiments was performed by the same person (CS).

Statistical analysis was performed using Fisher's exact test and independent samples t-test (StatSoft, Inc.). Differences in data were considered significant when $P<0.05$.

TABLE 2

Distribution of grades amongst thawed 2–4 cell embryos

| Embryo grade | Control (%) | GM-CSF (%) |
|---|---|---|
| A | 20 | 20 |
| B | 22 | 27 |
| C | 32 | 33 |
| D | 26 | 20 |
| N | 50 | 49 |

Grades are defined in Table 1.

Results

The rate and extent of development of 2–4 cell embryos to the blastocyst and hatching blastocyst stages was significantly increased by the addition of rhGM-CSF to culture medium (Table 3).

TABLE 3

Rate and extent of embryo development in the presence or absence of rhGM-CSF

| Expt | n | % BΦ Control | $T_{50}$ | % H | N | % BΦ RhGM-CSF | $T_{50}$ | % H |
|---|---|---|---|---|---|---|---|---|
| 1 | 16 | 38 | 122 | 50 | 15 | 60 | 121 | 89 |
| 2 | 16 | 38 | 116 | 50 | 16 | 81 | 98 | 100 |
| 3 | 18 | 17 | 127 | 33 | 18 | 83 | 105 | 53 |
| Total | 50 | 31 | 122 | 47 | 49 | 76[a] | 108[b] | 78[c] |

% BΦ = % of viable thawed 2–4 cells reaching blastocyst stage.
[a]p < 0.0001
$T_{50}$ = number of hours post-insemination at which 50% blastocysts develop.
[b]p = 0.0002 at 112h PI
% H = % of blastocysts which fully or partially hatch.
[c]p = 0.009

A comparison between the proportion of embryos reaching blastocyst stage and beyond in experiment 1 and 2 (culture media containing 5% FCS from day 5) and experiment 3 (serum-free media) are presented in Table 4. There are no significant differences between the two groups, showing that the beneficial effect of GM-CSF is not dependent on the presence of FCS.

TABLE 4

Percent embryos developing up to or beyond each developmental stage in experiment 1 and 2 (FCS added) compared with experiment 3 (no FCS added).

|  | N | % BΦ | % Exp BΦ | % Hatching | Attached |
|---|---|---|---|---|---|
| Control (exp 1 + 2) | 32 | 37 | 28 | 19 | 0 |
| GM-CSF (exp 1 + 2) | 31 | 71 | 68 | 68 | 38 |
| Control (exp 3) | 18 | 17 | 6 | 6 | 0 |
| GM-CSF (exp 3) | 18 | 83 | 61 | 44 | 22 |

BΦ = blastocyst; Exp BΦ = expanded blastocyst

Although fewer poor quality embryos (grades C & D) reach blastocyst stage than good quality (grades A & B), GM-CSF exerted a comparable effect in all groups, with similar or slightly higher increases in the proportion of poor compared with good quality embryos achieving blastocyst stage (FIG. 1).

Figure 2:
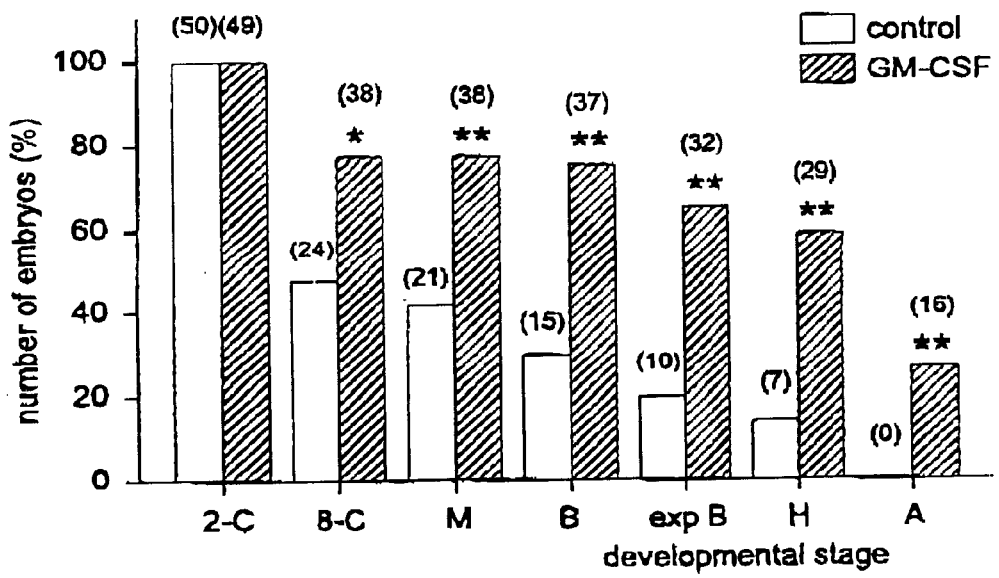
FIG. 2: The effect of GM-CSF on the development of embryos to blastocyst, hatching and attachment stages. Data is the number of embryos developed to or beyond each stage, from experiments 1, 2 and 3 combined, expressed as a percentage of the initial number of cleaved (2–4 cell) embryos. 2-C=2-cell embryos; 8-C=8-cell embryos; M=morulla; B=blastocyst; Exp B=expanded blastocyst; H=hatching; A=attached with trophectoderm outgrowth.
Figure 5:
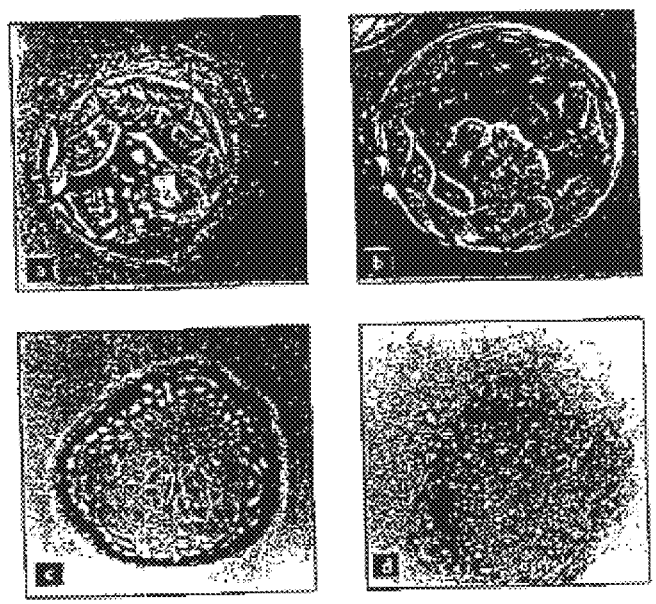
FIG. 5 The effect of GM-CSF on the rate of development of embryos to the blastocyst stage; (A) an early blastocyst (day 5, 112 h post-insemination) from the control group; (B) an expanded blastocyst (day 5, 112 h post-insemination) cultured in rhGM-CSF; (C) a fully hatched blastocyst attached to the culture dish (day 6, 144 h post-insemination); (D) an attached blastocyst cultured in rhGM-CSF showing trophectoderm outgrowth (arrow; day 8, 200 h post-insemination).

The majority of embryos grown in media alone were lost at the 4–16 cell stage. The beneficial effect of GM-CSF on blastocyst development appeared to result from rescue of this loss, with an 80% increase in the numbers of embryos reaching the morula stage of development (FIG. 2). Furthermore, the developmental potential of blastocysts was increased by culture in GM-CSF, since the rate of hatching was greater for embryos grown in GM-CSF. Similarly, blastocysts grown in GM-CSF (15/29), but not in control media (0/15), attached to the culture dish and showed trophoblast outgrowth (FIG. 2 and FIG. 5).

Figure 3:
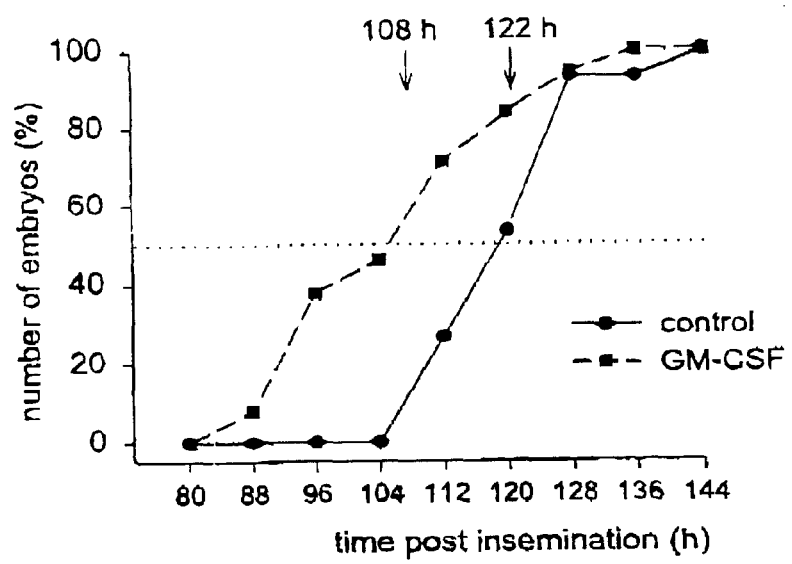
FIG. 3: The effect of GM-CSF on the rate of development of embryos to blastocyst. Data is the number of blastocysts at each time point, from experiments 1, 2 and 3 combined, expressed as a percentage of the total number of blastocysts at 144 h post insemination.

Finally, embryos cultured in the presence of rhGM-CSF had a significantly higher rate of development, with 50% blastocyst development achieved 14 hours earlier in GM-CSF compared with the control group (FIG. 3).

Conclusions

These results support the hypothesis that GM-CSF secreted into the female reproductive tract during early pregnancy promotes embryo growth and development. The addition of GM-CSF to culture media promotes the formation of blastocysts even with poor post thaw quality embryos. Our results also show a beneficial effect of GM-CSF on blastocyst expansion, hatching, attachment and trophectoderm outgrowth. Although the functional significance of hatching in vitro is unknown, blastocyst expansion is one of the best criteria for blastocyst viability and developmental potential.

The cleavage rate of embryos is suggested to be an indicator of embryo quality (Shoukir et al., 1997), and the rate of embryo development is known to be higher in vivo. Importantly, development of embryos to blastocysts was achieved significantly faster in the presence of rhGM-CSF.

EXAMPLE 2

Measurement of Embryonic Viability and Development—Variation of Media and Source of GM-CSF

Materials and Methods

The embryos used in this study were donated by couples, after ovarian stimulation and in vitro fertilisation, as described in Example 1. For culture experiments, embryos frozen at the 2–4 cell stage were thawed at or beyond their one year storage limit in liquid nitrogen. The blastocysts used for the differential staining experiment were cultured from excess embryos, surplus to treatment and freezing requirements.

Recombinant GM-CSF

Two different commercial sources of recombinant human (rh)GM-CSF were used in these experiments. A laboratory grade preparation was obtained from R&D Systems Europe Ltd, Oxon, UK, and a pharmaceutical grade preparation, Molgramostim (Leucomax) was obtained from Schering & Plough, Madison, N.J., USA. The biological activity of both recombinant cytokine preparations were measured in a bioassay employing a GM-CSF responsive cell line (human myeloid TF-1 cell line), as described in Example 1.

Embryo Thawing, Allocation and Culture

Frozen 2–4 cell embryos were thawed and allocated randomly to experimental groups as as described in Example 1. Embryo culture was performed as described in Example 1, in two different sequential media systems using two different commercial sources of rhGM-CSF. After thawing, the embryos were cultured first in G1.2 (Scandinavian IVF Science) or IVF-50. At 6–8 cell stage the embryos were transferred into G2.2 (Scandinavian IVF Science) or S2. The experiment included 6 groups: (a) G1.2/G2.2 alone, (b) G1.2/G2.2 containing 2 ng/ml rhGM-CSF (R&D Systems) (c) G1.2/G2.2 containing 2 ng/ml Molgramostim (Schering & Plough; diluted 1:75 000 from stock material), (d) IVF-50/S2 alone, (e) IVF-50/S2 containing 2 ng/ml rhGM-CSF (R&D Systems) (f) IVF-50/S2 containing 2 ng/ml Molgramostim. Developmental rate was scored every eighth hour until expanded blastocyst stage. Blastocysts were scored on day 5 at 120 h post-insemination according to criteria described previously (Dokras et al., 1993). Briefly, grade A blastocysts exhibited an expanded cavity with a distinct trophectoderm (TE) and an eccentrically located inner cell mass (ICM); grade B blastocysts were not yet expanded but otherwise morphologically identical to A; and grade C blastocysts exhibited poor morphology characterised by a number of degenerative foci in the ICM and TE and a poorly developed blastocoel cavity. Embryo scoring in each of the experiments was performed by the same person (CS).

Statistical analysis was performed using Fisher's exact test and independent samples t-test (StatSoft, Inc.). Differences in data were considered significant when P<0.05.

Differential Labelling of Blastocysts

Differential labelling was performed using a modification of a protocol described previously (Handyside and Hunter, 1984). Human blastocysts were cultured from excess embryos, surplus to treatment and freezing. On day 5 of culture (120–128 h post-insemination) the zona was removed in Acid Tyrodes solution containing 4 mg/ml PVP (360 000 Mw) and embryos were washed once in Gamete-100 (Scandinavian IVF Science) and three times in albumin-free S2 containing 4 mg/ml PVP (S2-PVP). The blastocysts were incubated in trinitro-benzene sulfonic acid (TNBS, Sigma Chemical Co., St Louis, Mo., USA; 10 mM in S2-PVP pH 8.5, 4° C./20 min in the dark) and washed three times in Gamete-100. TNBS-treated blastocysts were incubated in anti-dinitro-phenyl antibody (anti-DNP; Sigma, 0.2 mg/ml diluted in Gamete-100; 37° C. /30 min) Embryos were then washed and incubated in guinea pig complement serum (Sigma; diluted 1:10 in Gamete-100; 37° C./30 min). Embryos were washed again and labelled with flourochromes (Sigma; 0.05 mM bisbenzimide and 10 ug/ml propidium iodide in Gamete-100, 37° C./30 min). After extensive washing embryos were fixed briefly in 1% paraformaldehyde and 0.5% glutaraldehyde in PBS, mounted under cover-slips in 20% glycerol in PBS and examined by fluorescence microscopy using a 400 nm exitation filter. Nuclei stained pink were scored as lysed trophectoderm cells (TE) and blue nuclei were scored as viable inner cell mass cells (ICM).

Results

This experiment demonstrates the effect of culture media and source of recombinant cytokine on GM-CSF stimulated blastocyst development. Cytokine formulations in two different sequential culture media systems were found to have equivalent bioactivities in the TF-1 cell proliferation assay (data not shown). There were no significant differences between the blastulation rates achieved in the two different culture media systems (Table 5). Both the rate and extent of development of 2–4 cell embryos to blastocysts was significantly increased by the addition of 2 ng/ml rh GM-CSF. The effect was comparable in extent in both G1.2/G2.2 and IVF-50/S2 sequential media combinations. Furthermore, the improvement in blastocyst development was achieved irrespective of the formulation of recombinant cytokine. The results also show that although culture in rhGM-CSF gives rise to more blastocysts, the distribution in morphological grade was comparable in treatment and control groups (Table 5).

TABLE 5

The effect of culture media and source of recombinant cytokine on GM-CSF stimulated blastocyst development.

|  | N | % B ϕ | A/B/C (%) |
|---|---|---|---|
| G1.2/G2.2 alone | 23 | 30 | 57/29/14 |
| G1.2/G2.2 + rhGM-CSF (R&D) | 21 | 71** | 67/20/13 |
| G1.2/G2 + Molgramostim | 19 | 63* | 67/17/17 |
| IVF-50/S2 alone | 38 | 37 | 57/29/14 |
| IVF-50/S2 + rhGM-CSF (R&D) | 38 | 79*** | 67/26/7 |
| IVF-50/S2 + Molgramostim | 20 | 65* | 70/15/15 |

*P < 0.05;
**P < 0.01;
***P < 0.001

The Effect of Culture in GM-CSF on Blastomere Number and Allocation.

Figure 6:
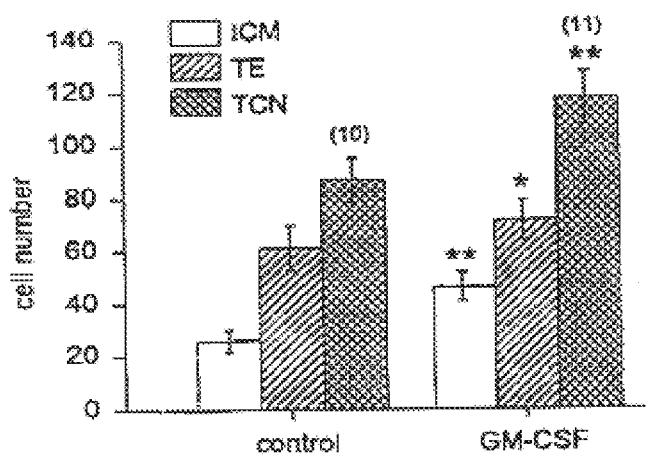
FIG. 6 The effect of GM-CSF on the number of total cells (TCN), inner cell mass (ICM) cells and trophectoderm (TE) cells in day 5 blastocysts (120–124 h post-insemination). Values are mean±SD of blastocysts cultured in 2 ng/ml rhGM-CSF (n=11) and blastocysts cultured in media alone (n=10).

To investigate the effect of culture with GM-CSF on cell number and allocation to inner cell mass and trophectoderm cell lineage, blastocysts cultured with and without rhGM-CSF were analysed by immunosurgery and differential staining. Blastocysts cultured in the presence of rhGM-CSF had a significantly higher total cell number compared to blastocysts cultured in media alone (FIG. 6). An increase in the number of trophectoderm cells, and particularly in the number of inner cell mass cells, each contributed to the greater cell number in GM-CSF stimulated blastocysts.

EXAMPLE 3

IVF Media

The techniques and media used for embryo culture in IVF procedures have not changed a great deal since the 1980s. These procedures are set out most particularly in Kerin et al (1983), Trouson et al (1980), Trouson et al (1982), and Quinn et al (1985) which references are incorporated herein by references in relation to those procedures.

The media in which this invention might be used can be any media suitable for use for the in vitro support of embryo development and growth. These media might include but are not limited to HTF medium (Quinn, 1985a), Modified Whittens medium (Trounson, 1984), whittinghams T6 medium (Trounson, 1984), Hams F10 (Trounson et al, 1982a), Earles solution (Edwards and Purdy, 1982), IVF50 (Scandinavian IVF Science), S2 (Scandinavian IVF Science), G1.2 (Scandinavian IVF Science) and G2.2 (Scandinavian IVF Science) which references are incorporated herein by references in relation to the media.

EXAMPLE 4

Method of IVF Treatment

IVF procedures have not changed a great deal since the 1980s. The procedures for IVF treatment used in this invention are standard procedures that are set out most particularly in Kerin et al (1983), Trouson et al (1980), Trouson et al (1982), and Quinn et al (1985) which references are incorporated herein by references in relation to those procedures.

EXAMPLE 5

The Expression of GM-CSF Receptors by Human Pre-implantation Embryos in Vitro

Material and Methods

The embryos used in this study were donated by couples, after ovarian stimulation and in vitro fertilsation, as described in Example 1. Excess human 2–4 cell embryos surplus to patients' requirements were cultured in 20 ml droplets of IVF-50 overlayed with paraffin oil. On day 3 (72 h post insemination) the embryos were transferred to S2. Embryos were collected at blastocyst stage of development. The embryos were washed in PBS, snap frozen in liquid nitrogen and stored at −70° C. prior to RNA extraction.

Total cellular RNA was extracted from human GM-CSF responsive myeloid cells (TF-1 cell line), and from two cohorts each of twenty blastocysts using a method described by (Arcellana-Panlilio & Schultz, 1993). Residual chromosomal DNA was removed by treatment with RNAse-free DNAse (Boehringer Mannheim) for 60 min at 37° C. First stand cDNA synthesis was achieved by reverse transcription (RT) of RNA primed with random hexamers using a Superscript RNase H-reverse transcriptase kit (Gibco) essentially according to the manufacturer's instructions. Detection of mRNA by RT-PCR was performed using primer pairs specific for the α-chain and β-chain of the GM-CSF receptor (GM-Rα and GM-Rβ), and β-actin (detailed in Table 7) and reagents supplied in receptor (GM-Rα and GM-Rβ), and β-actin (detailed in Table 7) and reagents supplied in a Taq DNA polymerase kit (Biotech Intenational Ltd., Perth), essentially as described previously. The number of cycles and annealing temperature used for each primer pair are also given in Table 7. To increase the sensitivity of the GM-Rβ PCR, a nested primer design was employed, wherein cDNA was amplified by 30 cycles with GM-Rb 'external' primers followed by 25 cycles with GM-Rβ 'internal' primers. Each PCR product was analysed by electrophoresis through a 2% agarose gel containing EtBr, and visualised by transillumination with UV-light. Gels were photographed and the size of the PCR products was verified by comparison of their relative mobility to molecular weight markers.

TABLE 7

Primer sequences

| Target | Genebank accession number | Primer sequence | Position in sequence | Cycle number/ annealing temp | Product size |
|---|---|---|---|---|---|
| β-actin | M12481 | 5' tgtgatggtgggtatgggtc | 48–67 | 35/ | 372 bp |
|  |  | 3' tagatgggcacagtgtgggt | 400–419 | 62° C. |  |
| GM-Rα | M64445 | 5' catgcttctcctggtgacaa | 162–161 | 40/ | 279 bp |
|  |  | 3' gtgactccttcatgcagaca | 421–440 | 60° C. |  |
| GM-Rβ | M59941/ M38275 | external: | 142–161 | 30/ | 428 bp |
|  |  | 5' ctacaccagccacatcacct | 550–569 | 65° C. |  |
|  |  | 3' agtcctgaagccgcttgtag | 239–258 | 25/ |  |
|  |  | internal: | 449–468 | 65° C. | 230 bp |
|  |  | 5' gagccagtgtcctgtgacct |  |  |  |
|  |  | 3' tggtcctggtcggtgctgat |  |  |  |

Results

Figure 4:
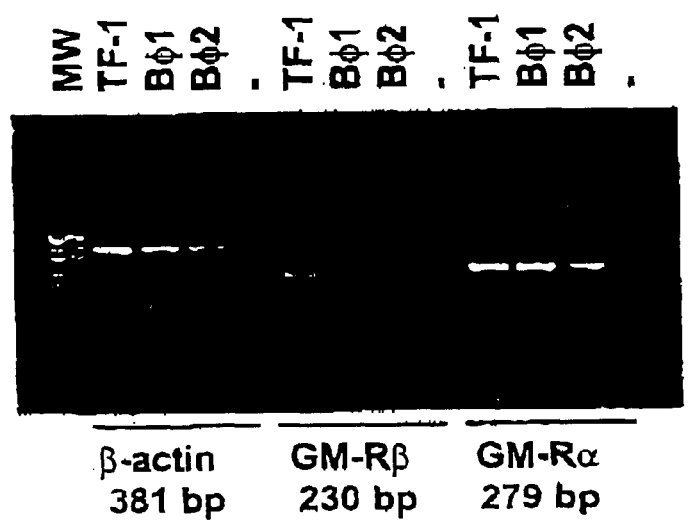
FIG. 4 RT-PCR analysis of GM-CSF receptor mRNA expression in human blastocysts. Total cellular RNA was extracted from TF-1 cells and each of two cohorts of blastocysts (B$\phi$1 and B$\phi$2), reverse transcribed by random priming and amplified by PCR with GM-R$\alpha$, GM-R$\beta$ or actin-specific primers using conditions listed in Table 7.

The expression of GM-CSF receptor expression by in vitro generated blastocysts was examined by RT-PCR. Each of two preparations of blastocysts were found to express mRNA for the a-chain of the GM-CSF receptor, but mRNA for the β-chain was not detected, even when a highly sensitive nested PCR protocol was used (FIG. 4).

Conclusions

Expression of GM-CSF receptor a-chain mRNA was detected in each of two blastocyst cDNA preparations. These results indicate that human blastocysts have the molecular capacity to bind and respond to GM-CSF. The expression of the a-subunit in the absence of the β-chain may benefit blastocyst glucose transport and thus optimist the culture environment. Increased glucose uptake is likely to promote blastomere metabolic activity, and hence cell division, and may also prolong cell survival through the prevention of apoptosis.

REFERENCES

Arcellana-Panlilio & Schultz, 1993. *Methods Enzymol.* 225; 303–28.
Armstrong & Chaouat, 1989. *Biol Reprod* 40; 466–474
de Moraes & Hansen. 1997, *Biol Reprod.* 57; 1060–1065
Ding et al., 1994 *Proc Natl Acad Sci USA*. 91(7); 2537–41
Drake & Head, 1994, *J Reprod Immunol* 26; 41–56
Dunglison et al., 1996, *Hum Reprod.* 11; 191 196
Edwards and Purdy, 1982, (eds) 1982 Human conception in vitro Academic Press, London
Giacomini et al., 1995. *Hum-Reprod.* 10, 3259–63
Hill et al., 1987. *J Immunol* 139; 2250–2254
Jokhi et al., 1994, 26; 147–164
Kerin et al, 1983, *Clin Reprod. Fertil.* 2; 129–142
Lea & Clark, 1993, *Biol Reprod* 48; 930–953
Lenton et al., 1988, *Ann NY Acad Sci*, 541; 498–509
Loke et al., 1992, *J Reprod Immunol*, 22; 33–45
Ménézo et al., 1990, *Biol Reprod*, 40; 301–306
Ménézo et al., 1992, *Hum Reprod*, 7; 101–106
Oliveness et al., 1955, *Hum Reprod*, 9; 2367–2373
Plachot et al. 1955 In Aburumieh et al (eds) IXth World Congress on In Vitro Fertilisation and Assisted Reproduction Monduzzi Editore, Bologna p 37
Quinn et al 1985, In Annals of N.Y. Acad. Sci. 442; 195–204.
Quinn et al 1985a, Fertil. amd Steril. 44; 493–498
Robertson et al., 1991, pp191–206 in Molecular and Cellular Immunobiology of the Maternal Fetal Interface, Wegmann et al eds Oxford University Press)
Robertson et al., 1992. *Biol Reprod* 46; 1069–79.
Robertson et al., 1996 *Biol Reprod* 54; 183–196.
Robertson et al., 1998 The effect of GM-CSF deficiency on early embryonic development in mice. Proceedings of the 29th Annual Conference of the Australian Society for Reproductive Biology. Shoukir et al., 1997. *Hum. Reprod.* 7: 1531–1536
Robertson et al., 1999 *Biol Reprod* 60; 251–261.
Tartakovsky & Ben-Yair, 1991. *Dev Biol* 146; 345–352
Trouson et al, 1980, Fertil. Steril. 34; 431–438
Trouson et al, 1982, J reprod. Fertil. 64; 285–294
Trounson et al 1982a) In: Edward and Prudy (eds) Human conception in vitro. Academic Press, London, p201–205
Trounson 1984. in Invitro Fertilization and Embryo Transfer, Churchill Livingstone, (Trounson & Wood eds) pp111–130
Weinberg et al., 1988, *Fert Steril*, 50; 993–5
Zhao & Chegini, 1994. *J Clin Endocrinol Metab.* 2; 662–5.

What is claimed is:

1. A method of growing preblastocyst human embryos, the method including the step of incubating the embryos in vitro in a culture medium containing an effective amount of human GM-CSF to increase the chance of implantation of the embryos, the amount of GM-CSF being sufficient to increase the proportion of blastocysts formed from preblastocyst embryos when compared to embryos incubated in a medium lacking GM-CSF.

2. The method of growing preblastocyst human embryos as in claim 1 wherein the embryos are contacted with GM-CSF at stage earlier than morula.

3. The method of growing preblastocyst human embryos as in claim 1 wherein the embryos are contacted with GM-CSF at the morula stage or earlier.

4. The method of growing preblastocyst human embryos as in claim 3 wherein the contact is within 2 days of fertilisation.

5. The method of growing preblastocyst human embryos as in claim 3 wherein the in vitro growth is continued until the blastocysts reach the day 5 to 6 stage.

6. The method of growing preblastocyst human embryos as in claim 5 wherein the embryo is cultured in a serum deprived medium including human GM-CSF until blastocyst stage is reached, and then transferred to a second medium including human GM-CSF for further culturing.

7. The method of growing preblastocyst human embryos as in claim 6 wherein the human GM-CSF is in purified form.

8. The method of growing preblastocyst human embryos as in claim 7 wherein the human GM-CSF is purified from a recombinant micro-organism.

9. The method of growing preblastocyst human embryos as in claim 1, wherein the medium is a serum deprived medium.

10. The method of growing preblastocyst human embryos as in claim 9 wherein the level of human GM-CSF in the medium is between 0.01 ng/ml and 5 ng/ml.

11. The method of growing preblastocyst human embryos as in claim 9, wherein more than about 60% of the preblastocysts form blastocysts.

12. The method of growing preblastocyst human embryos as in claim 9 wherein more than about 45% of the blastocysts formed are capable of fully or partially hatching.

13. The method of growing preblastocyst human embryos as in claim 9 wherein more than about 20% of the blastocysts formed are capable of attaching.

14. The method of growing preblastocyst human embryos as in claim 1, the step of incubating embryos continued until said embryos mature to blastocysts.

15. An IVF program comprising the steps of:
   contacting a human egg with a human sperm to form a conceptus
   growing the resulting conceptus in vitro in a chemically defined medium containing an effective amount of human GM-CSF to increase the chance of implantation of the embryos
   transferring the embryo into a compatible human uterus,
   wherein the amount of human GM-CSF is sufficient to increase the proportion of blastocysts formed from preblastocyst embryos when compared to culturing the resulting conceptus in a medium lacking GM-CSF.

16. The IVF program as in claim 15 wherein the embryo is cultured in a serum deprived medium including human GM-CSF until blastocyst stage is reached, and then transferred to a second medium including human GM-CSF for further culturing.

17. The IVF program as in either claim 16 wherein the human GM-CSF is in purified form.

18. The IVF program as in claim 17 wherein the human GM-CSF is purified from a recombinant micro-organism.

19. An IVF program as in claim 15 wherein the level of human GM-CSF in the medium is between 0.01 ng/ml and 5 ng/ml.

20. The IVF program as in claim 15 wherein the conceptus is grown in vitro from at least an 8 cell stage embryo until a blastocyst has formed.

* * * * *